United States Patent [19]

Maurer

[11] Patent Number: 4,686,290
[45] Date of Patent: * Aug. 11, 1987

[54] PREPARATION OF PYRIMIDYL PHOSPHORIC ACID DERIVATIVES AND INTERMEDIATES

[75] Inventor: Fritz Maurer, Wuppertal, Fed. Rep. of Germany

[73] Assignee: Bayer Aktiengesellschaft, Leverkusen, Fed. Rep. of Germany

[*] Notice: The portion of the term of this patent subsequent to May 12, 2004 has been disclaimed.

[21] Appl. No.: 743,452

[22] Filed: Jun. 11, 1985

[30] Foreign Application Priority Data

Jun. 27, 1984 [DE] Fed. Rep. of Germany ....... 3423623

[51] Int. Cl.⁴ ............... C07F 9/65; C07D 239/36; C07D 239/52; C07D 239/54
[52] U.S. Cl. .................. 544/243; 544/298; 544/318; 544/319
[58] Field of Search .............. 544/243, 298, 319, 318

[56] References Cited

U.S. PATENT DOCUMENTS

| | | | |
|---|---|---|---|
| 3,249,603 | 5/1966 | Bretschneider et al. | 544/319 X |
| 3,331,841 | 7/1967 | Priewe et al. | 544/298 |
| 3,907,797 | 9/1975 | Budesinsky et al. | 544/298 |
| 4,162,310 | 7/1979 | Maurer et al. | 514/86 |
| 4,429,125 | 1/1984 | Reifschneider | 544/243 |
| 4,444,764 | 4/1984 | Reifschneider et al. | 544/298 X |
| 4,558,039 | 12/1985 | Reifschneider et al. | 544/298 X |
| 4,612,375 | 9/1986 | Wade | 544/319 X |

FOREIGN PATENT DOCUMENTS 2365577 4/1978 France .
0028776 12/1964 Japan .................. 544/298

OTHER PUBLICATIONS

Greene, "Protective Groups in Organic Synthesis, John Wiley & Sons, New York, 1981, p. 97.
Chesterfield, et al., J. Chem. Soc. 1960, pp. 4590–4596.
McOmie, et al., J. Chem. Soc., 1963, pp. 5590–5593.
Umemoto, et al., Chemical Abstracts, vol. 79, 32082a (1973).
Hurst et al., "Pyrimidines. Part XIV. Synthesis of 2,5-Dihydroxypyrimdine", J. Chem. Soc. (Dec. 1965), pp. 7116–7118.
Abstract, Kaemmerer et al., "Halogen as a Readily Cleavable Protective Group for . . . ", Chem. Abs. vol. 86, (1977), No. 155305c, p. 440.

Primary Examiner—Nicholas S. Rizzo
Assistant Examiner—Diana G. Rivers
Attorney, Agent, or Firm—Sprung Horn Kramer & Woods

[57] ABSTRACT

$$HO-CH_2COOR^6 + CH_2=CH-OR^4 + HCOOR^7 +$$

VIII    IX    X

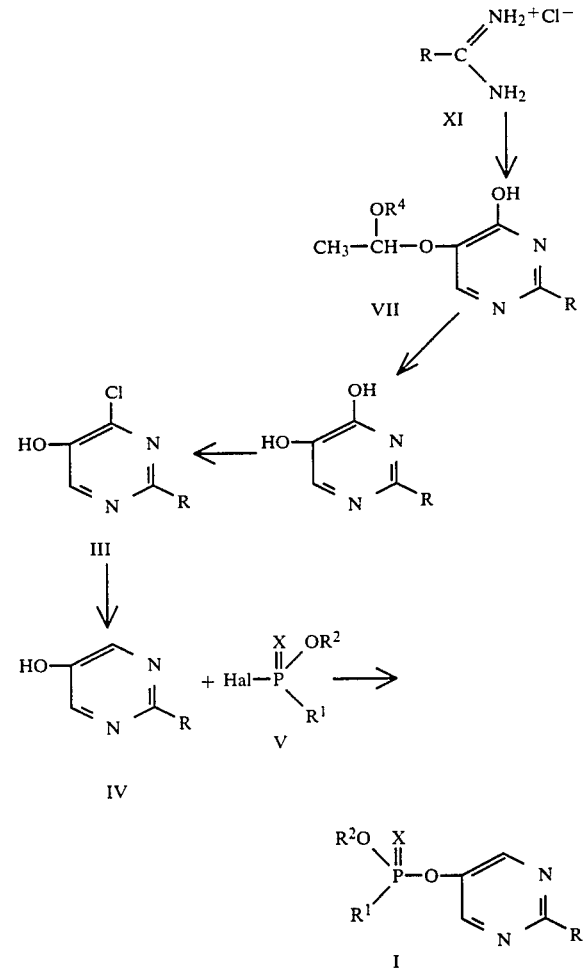

End products I are known insecticides. III and VII are new intermediates.

6 Claims, No Drawings

PREPARATION OF PYRIMIDYL PHOSPHORIC ACID DERIVATIVES AND INTERMEDIATES

The invention relates to a new process for the preparation of insecticidal pyrimidinyl phosphoric acid derivatives, to intermediates which can be used for carrying out the process, and to processes for the preparation of intermediates of this type.

It has already been disclosed that certain pesticidal pyrimidine esters of phosphoric acid are obtained when corresponding phosphoric ester chlorides are reacted with 5-hydroxypyrimidines [corresponding to U.S. Pat. No. 4,127,652 and DE-OS (German Published Specification) No. 2,706,127]. However, this method of preparation has only restricted utility for this purpose because of the lack of suitable starting compounds or because of unsatisfactory methods of preparation. Thus, there is a need for new intermediates and an appropriate process for the preparation of pyrimidine esters of phosphoric acid.

It has now been found that the compounds of the general formula I

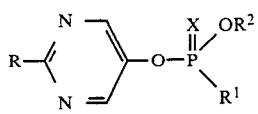

in which
R represents hydrogen, alkoxy, alkylamino, dialkylamino or optionally substituted radicals from the group comprising alkyl, cycloalkyl and aryl,
$R^1$ represents optionally substituted radicals from the group comprising alkyl, alkoxy, alkylthio, monoalkylamino or dialkylamino and phenyl,
$R^2$ represents optionally substituted alkyl, and
X represents oxygen or sulphur,
are obtained when
(a) compounds of the general formula II

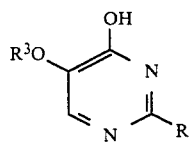

in which
R has the abovementioned meaning, and
$R^3$ represents hydrogen or a group

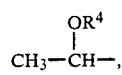

$R^4$ representing alkyl,
are reacted with halogenating agents in the presence of N,N-disubstituted amides and, where appropriate, in the presence of diluents, at temperatures between 10° C. and 80° C., to give the compounds of the general formula III

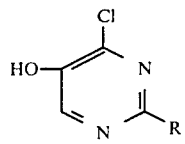

in which
R has the abovementioned meaning,
and then
(b) the compounds of the general formula III, where appropriate after their isolation, are reacted with hydrogen in the presence of hydrogenation catalysts, in the presence of acid acceptors and in the presence of diluents, at temperatures between 20° C. and 150° C., to give the compounds of the general formula IV

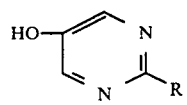

in which
R has the abovementioned meaning,
and then
(c) the compounds of the general formula IV, where appropriate after their isolation, are reacted with compounds of the general formula V

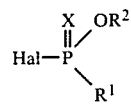

in which
Hal represents halogen, and
X, $R^1$ and $R^2$ have the abovementioned meaning,
where appropriate in the presence of an acid-binding agent and, where appropriate, in the presence of a solvent, and the compounds of the general formula I are isolated.

It is possible in a variant of the abovementioned process to carry out the preparation of the compounds of the general formula II (or VII) beforehand, it then being possible optionally to use the latter without their being isolated.

It is possible by this process to prepare the compounds of the formula I in a straightforward manner and in good purity and yield. The process has very wide utility in respect of the nature of the desired substituents. Furthermore, the compounds which are to be used as intermediates are stable and can easily be stored and manipulated.

Preferred substituents and ranges of the radicals detailed in the formulae mentioned above and below are illustrated by the following:

Alkoxy R represents straight-chain or branched alkoxy having, preferably, 1 to 12, in particular 1 to 6, and particularly preferably 1 to 4, carbon atoms. Examples which may be mentioned are methoxy, ethoxy, n-propoxy, i-propoxy, n-butoxy, i-butoxy, sec.-butoxy and tert.-butoxy.

Monoalkylamino or dialkylamino R represents an amino group having 1 or 2 alkyl groups, preferably 2 alkyl groups, each of which can be straight-chain or branched and which preferably contain 1 to 5, in particular 1 to 3, carbon atoms, mention being made of methyl, ethyl, n- and i-propyl. Examples which may be detailed are dimethylamino, diethylamino, di-n-propylamino and di-i-propylamino.

Optionally substituted alkyl R is represented by straight-chain or branched alkyl having 1 to 20, preferably 1 to 12, in particular 1 to 6, and particularly preferably 1 to 4, carbon atoms. Examples which may be mentioned are optionally substituted methyl, ethyl, n-propyl, i-propyl, n-butyl, sec.-butyl, i-butyl, tert.-butyl, n-pentyl, i-pentyl and tert.-pentyl.

Optionally substituted cycloalkyl R is represented by cycloalkyl having, preferably, 3 to 8, in particular 3, 5 or 6, carbon atoms. Examples which may be mentioned are optionally substituted cyclopropyl, cyclobutyl, cyclopentyl, cyclohexyl and cycloheptyl.

Optionally substituted aryl R is represented by aryl having, preferably, 6 to 10 carbon atoms in the aryl moiety. Examples which may be mentioned are optionally substituted phenyl or naphthyl, in particular phenyl.

The substituted radicals mentioned in the definition of R can carry one or more, preferably 1 to 3, in particular 1 or 2, identical or different substituents. The following substituents may be detailed for alkyl, cycloalkyl and aryl as examples:

Alkoxy and alkylsulphonyl having 1 to 4 carbon atoms, such as methoxy, ethoxy, n-propoxy, i-propoxy, n-butoxy, i-butoxy, sec.-butoxy, tert.-butoxy, methylsulphonyl, ethylsulphonyl, n-propylsulphonyl, i-propylsulphonyl, n-butylsulphonyl, i-butylsulphonyl and tert.-butylsulphonyl.

$C_1-C_4$-Alkyl, such as methyl, ethyl, n-propyl, i-propyl, n-butyl, i-butyl, sec.-butyl and tert.-butyl, are also suitable as aryl substituents and cycloalkyl substituents.

Preferably

R represents hydrogen, alkoxy having 1 to 12 carbon atoms, monoalkylamino or dialkylamino having 1 to 6 carbon atoms in each alkyl moiety, alkyl which has 1 to 12 carbon atoms and is optionally substituted by $C_1-C_4$-alkoxy or $C_1-C_4$-alkylsulphonyl, cycloalkyl which has 3 to 8 carbon atoms and is optionally substituted by $C_1-C_4$-alkyl, and aryl which has 6 to 10 carbon atoms and is optionally substituted by $C_1-C_4$-alkyl, $C_1-C_4$-alkoxy or $C_1-C_4$-alkylsulphonyl.

Particularly preferably

R represents hydrogen, alkoxy having 1 to 6 carbon atoms, monoalkylamino or dialkylamino having 1 to 4 carbon atoms in each alkyl moiety, or alkyl which has 1 to 6 carbon atoms and is optionally substituted by methoxy, ethoxy, methylsulphonyl or ethylsulphonyl, cycloalkyl which has 3 to 6 carbon atoms and is optionally substituted by methyl or ethyl, and phenyl which is optionally substituted by methyl, ethyl, methoxy, ethoxy, methylsulphonyl or ethylsulphonyl. R very particularly preferably represents methyl, isopropyl and t-butyl.

The optionally substituted alkyl groups $R^1$ and $R^2$ preferably contain 1 to 6, in particular 1 to 4, and particularly preferably 1 or 2, carbon atoms. Examples which may be mentioned are methyl, ethyl, n- and i-propyl, n-, i-, s- and t-butyl.

The alkyl groups in the optionally substituted alkylamino and dialkylamino groups $R^1$ preferably have the meaning indicated above as preferable for the alkyl groups $R^1$ and $R^2$. Examples which may be detailed are methyl-, ethyl-, n- and i-propylamino and dimethyl-, di-ethyl- and methyl-ethyl-amino.

The alkoxy and alkylthio radicals $R^1$ preferably contain 1 to 6, in particular 1 to 4, and particularly preferably 1 or 2, carbon atoms. Examples which may be mentioned are methoxy, ethoxy, n- and i-propoxy, and methylthio, ethylthio and n- and i-propylthio.

The optionally substituted radicals $R^1$ and $R^2$ can carry one or more, preferably 1 to 3, in particular 1 or 2, identical or different substituents. Examples of substituents which may be listed are: alkyl (does not apply to the case where $R^1$ or $R^2$ represents alkyl) preferably having 1 to 4, in particular 1 or 2, carbon atoms, such as methyl, ethyl, n- and i-propyl, and n-, i-, s- and t-butyl; alkoxy preferably having 1 to 4, in particular 1 or 2, carbon atoms, such as methoxy, ethoxy, n- and i-propyloxy and n-, i-, s- and t-butyloxy; alkylthio preferably having 1 to 4, in particular 1 or 2, carbon atoms, such as methylthio, ethylthio, n- and i-propylthio and n-, i-, s- and t-butylthio; halogen, preferably fluorine, chlorine, bromine and iodine, in particular chlorine and bromine; cyano and nitro.

Alkyl $R^4$ preferably represents $C_1-C_4-$, in particular $C_1-C_2-$, alkyl, examples which may be mentioned being methyl, ethyl, n- and i-propyl and n-, i-, s- and t-butyl.

Hal in the general formula V represents fluorine, chlorine, bromine and iodine, preferably fluorine, chlorine and bromine, in particular chlorine.

The compounds of the formula II in which $R^3$ represents hydrogen, which are to be used in process step (a), are known and/or can be prepared in a straightforward manner by known methods from 5-alkoxy-4-hydroxypyrimidines of the formula VI

 (VI)

in which

R has the abovementioned meaning, and $R^5$ represents $C_1-C_4$-alkyl, and strong acids such as, for example, hydrobromic acid or concentrated hydrochloric acid, at temperatures between 20° C. and 140° C. (see J. Chem. Soc. 1963, 5590 and the preparation examples).

The compounds of the formula VI are known and/or can be prepared by known methods (see DE-OS (German Published Specification) No. 2,639,256 and the preparation examples). They can also be obtained by the same method from the compounds of the general formula VII which are described below.

The compounds of the formula II in which $R^3$ represents the group

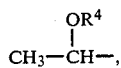

which are to be used in process step (a), are new and are described below by the general formula VII

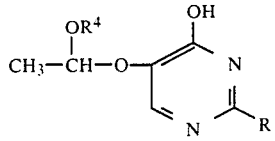 (VII)

in which

R and R⁴ have the abovementioned meaning.

The compounds of the general formula VII and the following process for their preparation are part of the present invention.

It has been found that the new 4-hydroxypyrimidine derivatives of the general formula VII

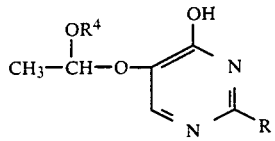 (VII)

in which

R and R⁴ have the abovementioned meaning, are obtained when hydroxyacetic esters of the general formula VIII

HO—CH$_2$COOR$^6$ (VIII)

in which

R$^6$ represents C$_1$-C$_4$-alkyl, are reacted, in the presence of catalysts, with vinyl ethers of the formula IX

CH$_2$=CH—OR$^4$ (IX)

in which

R$^4$ has the abovementioned meaning,
with further reaction with formic esters of the formula X

HCOOR$^7$ (X)

in which

R$^7$ represents C$_1$-C$_4$-alkyl,
in the presence of a base, and then with amidine hydrochlorides of the general formula XI

 (XI)

in which

R has the abovementioned meaning,
in the presence of bases and in the presence of diluents, at temperatures between 15° C. and 60° C.

It is surprising that the new 4-hydroxypyrimidine derivatives of the general formula VII can be obtained in good yields and in high purity by the process according to the invention, since it was to be expected that juxtaposition of the abovementioned reaction steps, without isolation and purification of the intermediates, would not lead to the desired products or, because of side reactions in individual steps, would lead to only small yields of contaminated compounds.

Thus, the new compounds of the general formula VII can be very easily obtained by the process according to the invention and are especially suitable for use in process step (a).

When, in the process according to the invention for the preparation of the compounds of the general formula VII, butyl glycolate, ethyl vinyl ether, methyl formate and isobutyramidine hydrochloride are used as the starting materials, then the reaction can be outlined by the scheme below:

HO—CH$_2$COOC$_4$H$_9$ + CH$_2$=CH—OC$_2$H$_5$ + HCOOCH$_3$ +

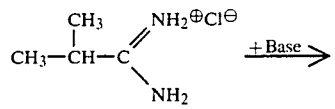

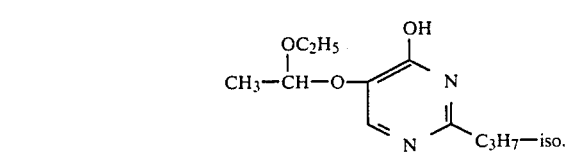

The hydroxyacetic esters to be used as starting materials in the process according to the invention are defined by formula VIII.

Examples which may be mentioned for compounds of the formula VIII are the following compounds: methyl, ethyl, n-propyl, i-propyl, n-butyl, i-butyl, sec.-butyl and tert.-butyl hydroxyacetate.

The vinyl ethers which are also to be used as starting materials for the process according to the invention are defined by formula IX.

Examples of compounds of the formula IX which may be mentioned are: methyl, ethyl, n-propyl, i-propyl, n-butyl, i-butyl, sec.-butyl and tert.-butyl vinyl ether.

The formic esters which are also be used as starting materials are defined by formula X.

Examples of compounds of the formula X which may be mentioned are: methyl, ethyl, n-propyl, i-propyl, n-butyl, i-butyl, sec.-butyl and tert.-butyl formate.

The amidine hydrochlorides which are also to be used as starting materials for the process according to the invention are defined by formula XI.

Examples of compounds of the formula XI which may be mentioned are the following compounds:

TABLE 1

 (XI)

| R | R |
|---|---|
| H | OC$_2$H$_5$ |
| CH$_3$ | OC$_3$H$_7$—n |
| C$_2$H$_5$ | OC$_3$H$_7$—iso |
| C$_3$H$_7$—n | —CH$_2$OCH$_3$ |
| C$_3$H$_7$—iso | —CH$_2$CH$_2$OCH$_3$ |
| C$_4$H$_9$—n | —CH$_2$OC$_2$H$_5$ |
| C$_4$H$_9$—iso | —CH$_2$CH$_2$OC$_2$H$_5$ |
| C$_4$H$_9$—sec | —CH$_2$SO$_2$CH$_3$ |
| C$_4$H$_9$—tert | —CH$_2$CH$_2$SO$_2$CH$_3$ |
| C$_5$H$_{11}$—n | —CH$_2$CH$_2$SO$_2$C$_2$H$_5$ |
| C$_5$H$_{11}$—tert | —N(CH$_3$)$_2$ |
| OCH$_3$ | —N(C$_2$H$_5$)$_2$ |

TABLE 1-continued

| R | R |
|---|---|
| 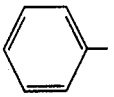 |  |
| 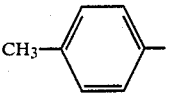 | 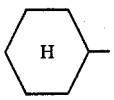 |
| 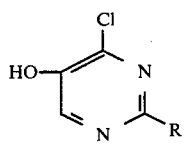 | |

The compounds of the formulae VIII, IX, X and XI are known and/or can be prepared by straightforward and known methods (see, for example, U.S. Pat. No. 4,012,506; German Pat. No. 584,840; Liebigs Ann. Chem. 601, 84 (1956); "Organic Functional Group Preparations" Vol. III, pages 205-240, Academic Press 1972).

The process according to the invention for the preparation of the compounds of the general formula VII is preferably carried out in the presence of diluents. Suitable and preferred diluents are: alcohols, such as methanol, ethanol, n- and i-propanol and tert.-butanol, aliphatic and aromatic, optionally halogenated, hydrocarbons, such as pentane, hexane, heptane, cyclohexane, petroleum ether, gasoline, ligroin, benzene, toluene, xylene, methylene chloride, ethylene chloride, chloroform, carbon tetrachloride, chlorobenzene and o-dichlorobenzene, ethers, such as diethyl and dibutyl ethers, glycol dimethyl ether and diglycol dimethyl ether, tetrahydrofuran and dioxane, ketones, such as acetone, methyl ethyl, methyl isopropyl and methyl isobutyl ketones, esters, such as methyl and ethyl acetate, nitriles, such as, for example, acetonitrile and propionitrile, amides, such as, for exmple, dimethylacetamide and N-methylpyrrolidone, and tetramethylene sulphone.

It is possible to use as bases for the process according to the invention virtually all acid-binding agents which are customarily employed. These include, in particular: alkali metal and alkaline earth metal hydroxides and oxides, such as sodium and potassium hydroxides and, in particular, lithium hydroxide, as well as calcium oxide or calcium hydroxide, alkali metal and alkaline earth metal carbonates, such as sodium, potassium and calcium carbonate, alkali metal alcoholates, such as sodium methylate, ethylate and tert.-butylate, also aliphatic, aromatic or heterocyclic amines, such as triethylamine, dimethylaniline, dimethylbenzylamine, pyridine, diazabicyclooctane and diazabicycloundecene.

The catalysts used are primarily acid catalysts, such as organic sulphonic acids, preferably aromatic sulphonic acids, such as toluenesulphonic acid.

The reaction temperatures can be varied within a relatively wide range. In general, the process is carried out between $-15°$ C. and $+70°$ C., preferably at $-10°$ C. to $+60°$ C. The process according to the invention is generally carried out under atmospheric pressure.

The starting materials are usually used in equimolar amounts to carry out the process according to the invention. An excess of either of the components in the reaction has no essential advantage. The working up and the isolation, where it is desired, are carried out by customary methods.

In process step (a), the compounds of the general formula II (or VII) are converted, where appropriate without being isolated, into the new compounds of the general formula III. The compounds of the general formula III and the process for their preparation by process step (a) are a part of the present invention.

It has been found that the new 4-chloro-5-hydroxypyrimidines of the general formula III

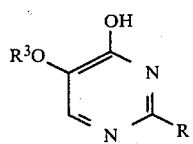

in which
R has the abovementioned meaning,
are obtained when pyrimidine derivatives of the general formula II

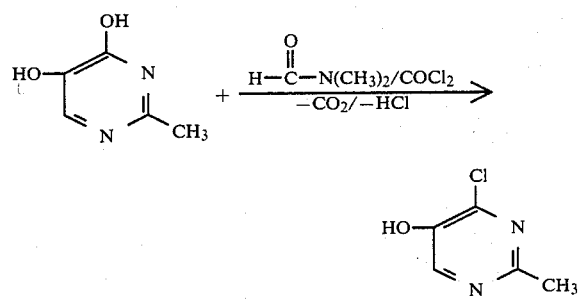

in which
R and $R^3$ have the abovementioned meaning,
are reacted with halogenting agents in the presence of N,N-disubstituted amides and, where appropriate, in the presence of diluents, at temperatures between $10°$ C. and $80°$ C.

It has to be denoted surprising that the new 4-chloro-5-hydroxypyrimidines are obtained in good yields and high purity by the process according to the invention, since it was to be exposed that, under the reaction conditions, the radical $-OR^3$ would also be attacked and/or, because of the presence of substituted amides, for example formylpyrimidines ("Vilsmeyer reaction") would be produced.

When 4,5-dihydroxy-2-methylpyrimidine is used as starting material and phosgene, in the presence of dimethylformamide, is used as the halogenating agent in the process according to the invention, then the reaction can be outlined by the equation below:

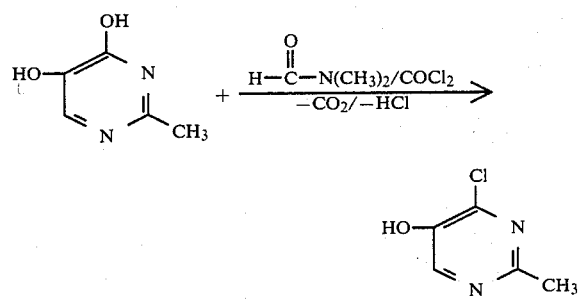

When 2-tert.-butyl-5-(1-ethoxyethoxy)-4-hydroxypyrimidine is used as starting material and phosgene, in the presence of dimethylformamide, is used as the halogenating agent in the process according to the invention, then the reaction can be outlined by the equation below:

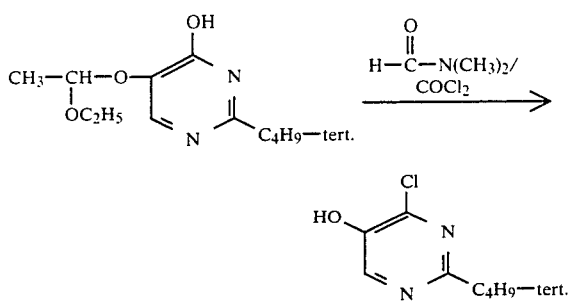

Examples of the starting compounds of the general formula (II) which may be listed are the following compounds:

TABLE 2

$$\underset{R^3O}{\overset{OH}{\bigvee}}\underset{N}{\overset{N}{\bigvee}}R \quad (II)$$

$R^3 = H, CH_3-\underset{OC_2H_5}{\overset{|}{CH}}-, CH_3-\underset{OCH_3}{\overset{|}{CH}}-$ or $CH_3-\underset{OC_3H_7}{\overset{|}{CH}}-$

| R | R |
|---|---|
| H | $OC_2H_5$ |
| $CH_3$ | $OC_3H_7$—n |
| $C_2H_5$ | $OC_3H_7$—iso |
| $C_3H_7$—n | —$CH_2OCH_3$ |
| $C_3H_7$—iso | —$CH_2CH_2OCH_3$ |
| $C_4H_9$—n | —$CH_2OC_2H_5$ |
| $C_4H_9$—iso | —$CH_2CH_2OC_2H_5$ |
| $C_4H_9$—sec | —$CH_2SO_2CH_3$ |
| $C_4H_9$—tert | —$CH_2CH_2SO_2CH_3$ |
| $C_5H_{11}$—n | —$CH_2CH_2SO_2C_2H_5$ |
| $C_5H_{11}$—tert | —$N(CH_3)_2$ |
| $OCH_3$ | —$N(C_2H_5)_2$ |
| cyclopropyl | phenyl |
| cyclopentyl | 4-methylphenyl |
| cyclohexyl-H | |

The process according to the invention for the preparation of the compounds of the general formula III, or process step (a), is preferably carried out in the presence of diluents. Suitable diluents are inert organic solvents. These include: benzene, chlorobenzene, o-dichlorobenzene, methylene chloride, ethylene chloride, chloroform, carbon tetrachloride and amides such as, for example, dimethylformamide, N-methylformamide and N-methylpyrrolidone.

The halogenating agents which are preferably used for the process according to the invention are: phosphorus oxychloride, phosphorus trichloride, oxalyl chloride, phosgene or thionyl chloride.

Suitable and preferred N,N-disubstituted amides are: dimethylformamide, N-methylformanilide, N-methylpyrrolidone or N-methylpiperidone.

The process according to the invention is generally carried out at temperatures between 10° C. and 80° C. The range between 20° C. and 60° C. is preferred. The reactions are generally carried out under atmospheric pressure.

To carry out the process according to the invention, 1 to 3 moles, preferably 1.2 to 2 moles, of halogenating agent and 1 to 3 moles, preferably 1.2 to 2 moles, of N,N-disubstituted amide are used for 1 mole of the compound of the formula II. The working up and isolation, where it is desired, of the compounds of the general formula III is carried out by customary methods.

Examples of compounds of the formula III which can be obtained according to the invention and which may be listed are the following:

TABLE 3

$$\underset{HO}{\overset{Cl}{\bigvee}}\underset{N}{\overset{N}{\bigvee}}R \quad (III)$$

| R | R |
|---|---|
| H | —$CH_2CH_2OCH_3$ |
| $CH_3$ | —$CH_2OC_2H_5$ |
| $C_2H_5$ | —$CH_2CH_2OC_2H_5$ |
| $C_3H_7$—n | —$CH_2SO_2CH_3$ |
| $C_3H_7$—i | —$CH_2CH_2SO_2CH_3$ |
| $C_4H_9$—sec. | —$CH_2CH_2SO_2C_2H_5$ |
| $C_4H_9$—tert. | —$N(CH_3)_2$ |
| $C_5H_{11}$—n | —$N(C_2H_5)_2$ |
| $C_5H_{11}$—tert. | cyclopropyl |
| $OCH_3$ | cyclopentyl |
| $OC_2H_5$ | cyclohexyl-H |
| $OC_3H_7$—n | —$CH_2OCH_3$ |
| $OC_3H_7$—i | 4-methylphenyl |

The compounds of the general formula IV which are to be used in process step (c) are known or can be prepared by generally known methods.

Thus, it has already been disclosed that 5-hydroxypyrimidines are obtained when 5-methoxypyrimidines are reacted under basic conditions in autoclaves at temperatures between 180° C. and 200° C. (see, for example, DE-OS (German Published Specification) No. 2,643,262 and Coll. Czech. Chem. Comm. 40, 1078 ff (1975)). The disadvantages of these processes are that the yields and the purity of the reaction products are frequently unsatisfactory and, moreover, extreme reaction conditions are necessary.

It has also been disclosed that the 5-hydroxypyrimidines can also be prepared from 5-methoxypyrimidines in the presence of alkali metal hydroxides and glycol. Temperatures of about 200° C. are necessary for this process. Other disadvantages are the elaborate work-up of the final products and the moderate yields (see, for example, J. Chem. Soc. 1960, 4590 ff and Chem. Ber. 95, 803 ff (1962)). In addition, the procedure in high-boiling polar solvents such as glycol makes special efforts in waste-water purification necessary.

It has been found that 5-hydroxypyrimidines of the general formula IV

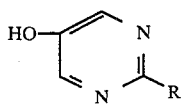

(IV)

in which

R has the abovementioned meaning, are obtained when substituted 4-chloropyrimidine derivatives of the formula III

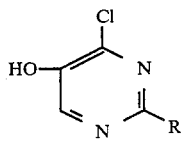

(III)

in which

R has the abovementioned meaning, are reacted with hydrogen in the presence of hydrogenation catalysts, in the presence of acid acceptors, and in the presence of diluents, at temperatures beween 20° C. and 150° C.

Surprisingly, using this process, which corresponds to process step (b) and which is part of the present invention, it is possible to obtain under relatively mild conditions the 5-hydroxypyrimidines of the general formula IV in good yield and in very high purity. Further advantages of the process are the recovery of the catalysts and the use of low-cost and more environmentally acceptable diluents.

When, for example, 4-chloro-5-hydroxypyrimidine and Raney nickel, as the catalyst, are used for the process according to the invention, then the reaction can be outlined by the equation below:

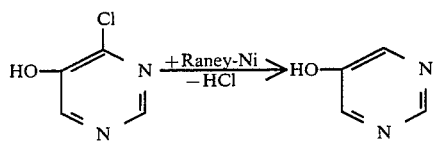

Water is preferably used as the solvent for the preparation of the compounds of the general formula IV from the compounds of the general formula III.

Suitable acid acceptors for the process according to the invention are all customarily utilizable inorganic and organic bases. These include, preferably, alkali metal carbonates, such as, for example, sodium and potassium carbonate; alkali metal hydroxides, such as, for example, sodium hydroxide; alkali metal alcoholates, such as, for example, sodium and potassium methylate and ethylate; and lower tertiary alkylamines, cycloalkylamines and aralkylamines, such as, in particular, triethylamine.

The process according to the invention is carried out in the presence of a hydrogenation catalyst. Neutral metal catalysts such as Raney nickel, Raney cobalt or palladium, where appropriate on customary support materials, such as, for example, active charcoal, are preferably used.

The reaction temperatures for carrying out the process according to the invention can be varied within a relatively wide range. In general, the process is carried out between 20° C. and 150° C., preferably between 20° C. and 100° C., in particular between 40° C. and 80° C.

The process according to the invention is generally carried out under elevated pressure, preferably between 5 and 60 bar, in particular between 7 and 40 bar.

To carry out the process according to the invention, between 1 and 5 moles, preferably between 1.2 and 3 moles, of acid acceptor and between 1 and 100 g, preferably between 5 and 50 g, of catalyst are used for 1 mole of 4-chloropyrimidine derivative of the formula III.

The starting materials of the formula III, the acid acceptor, the catalyst and the diluent are mixed and, during heating to the required temperature, hydrogen is injected. Hydrogen is injected at constant temperature until the end of the reaction is indicated by the pressure remaining constant.

Examples of compounds of the general formula IV which can be obtained according to the invention and which may be listed are the following:

TABLE 4

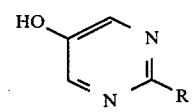

(IV)

| R | R |
|---|---|
| H | $OC_2H_5$ |
| $CH_3$ | $OC_3H_7$—n |
| $C_2H_5$ | $OC_3H_7$—iso |
| $C_3H_7$—n | —$CH_2OCH_3$ |
| $C_3H_7$—iso | —$CH_2CH_2OCH_3$ |
| $C_4H_9$—n | —$CH_2OC_2H_5$ |
| $C_4H_9$—iso | —$CH_2CH_2OC_2H_5$ |
| $C_4H_9$—sec | —$CH_2SO_2CH_3$ |
| $C_4H_9$—tert | —$CH_2CH_2SO_2CH_3$ |
| $C_5H_{11}$—n | —$CH_2CH_2SO_2C_2H_5$ |
| $C_5H_{11}$—tert | —$N(CH_3)_2$ |
| $OCH_3$ | —$N(C_2H_5)_2$ |

 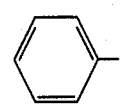

TABLE 4-continued

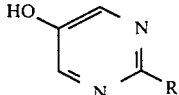

| R | R |
|---|---|
| cyclopentyl | CH$_3$-C$_6$H$_4$- |
| C$_6$H$_5$- (H-phenyl) | |

These compounds can be used in, for example, process step (c).

In process step (c), the compounds of the general formula I are obtained from the compounds of the general formulae IV and V.

When, for example, O-ethyl O-isopropyl thionophosphoric chloride and 5-hydroxy-2-phenylpyrimidine are used as starting materials in process step (c), then the corresponding reaction can be outlined by the equation below:

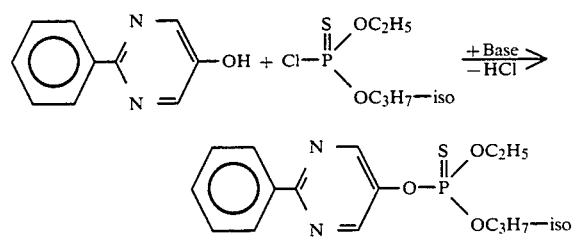

The starting materials of the general formula V to be used in process step (c) are known and can readily be prepared industrially by processes and methods known from the literature. Examples of these which may be specifically mentioned are: O,O-dimethyl, O,O-diethyl, O,O-di-n-propyl, O,O-di-iso-propyl, O,O-di-n-butyl, O,O-di-iso-butyl, O,O-di-sec.-butyl, O-methyl O-ethyl, O-methyl O-n-propyl, O-methyl O-iso-propyl, O-methyl O-n-butyl, O-methyl O-iso-butyl, O-methyl O-sec.-butyl, O-ethyl O-n-propyl, O-ethyl O-iso-propyl, O-ethyl O-n-butyl, O-ethyl O-sec.-butyl, O-ethyl O-iso-butyl, O-n-propyl O-butyl and O-iso-propyl O-butyl phosphoric chloride and the corresponding thiono analogues, also O,S-dimethyl, O,S-diethyl, O,S-di-n-propyl, O,S-di-iso-propyl, O,S-di-n-butyl, O,S-di-iso-butyl, O-ethyl S-n-propyl, O-ethyl S-iso-propyl, O-ethyl S-n-butyl, O-ethyl S-sec.-butyl, O-n-propyl S-ethyl, O-n-propyl S-iso-propyl, O-n-butyl S-n-propyl and O-sec.-butyl S-ethyl thiolphosphoric chloride and the corresponding thio analogues, also O-methyl, O-ethyl, O-n-propyl, O-iso-propyl, O-n-butyl, O-iso-butyl and O-sec.-butyl methane- or ethane-, n-propane-, iso-propane-, n-butane, iso-butane-, sec.-butane- and phenyl-phosphonic chloride and the corresponding thiono analogues, and O-methyl N-methyl, O-methyl N-ethyl, O-methyl N-n-propyl, O-methyl N-iso-propyl, O-ethyl N-methyl, O-ethyl N-ethyl, O-ethyl N-n-propyl, O-ethyl N-iso-propyl, O-n-propyl N-methyl, O-n-propyl N-ethyl, O-n-propyl N-n-propyl, O-n-propyl N-iso-propyl, O-iso-propyl N-methyl, O-iso-propyl N-ethyl, O-iso-propyl N-n-propyl, O-iso-propyl N-iso-propyl, O-n-butyl N-methyl, O-n-butyl N-ethyl, O-n-butyl N-n-propyl, O-n-butyl N-iso-propyl, O-iso-butyl N-methyl, O-iso-butyl N-ethyl, O-iso-butyl N-n-propyl, O-iso-butyl N-iso-propyl, O-sec.-butyl N-methyl, O-sec.-butyl N-ethyl, O-sec.-butyl N-n-propyl and O-sec.-butyl N-iso-propyl amidophosphoric chloride and the corresponding thiono analogues.

Process step (c) for the preparation of the compounds of the general formula I is preferably carried out with the additional use of suitable solvents and diluents. Virtually all inert organic solvents are suitable for this. These include, in particular, aliphatic and aromatic, optionally chlorinated, hydrocarbons, such as benzene, toluene, xylene, gasoline, methylene chloride, chloroform, carbon tetrachloride and chlorobenzene, or ethers, such as diethyl and dibutyl ethers and dioxane, also ketones, for example acetone, methyl ethyl, methyl isopropyl and methyl isobutyl ketones, also nitriles, such as acetonitrile and propionitrile.

All customary acid-binding agents can be used as acid acceptors. Alkali metal carbonates and alcoholates have proved particularly useful, such as sodium and potassium carbonate, and potassium tert.-butylate, also aliphatic, aromatic or heterocyclic amines, for example triethylamine, trimethylamine, dimethylaniline, dimethylbenzylamine and pyridine.

The reaction temperature can be varied within a relatively wide range. In general, the process is carried out between 0° and 100° C., preferably at 20° to 60° C.

The reaction is generally allowed to take place under atmospheric pressure.

To carry out process step (c), the equivalent ratio of the starting materials is usually employed. An excess of either of the components has no essential advantage. The reactants are usually mixed in one of the solvents listed above, in the presence of an acid-binding agent, and stirred for one or more hours at elevated temperature to complete the reaction. Then an organic solvent, for example toluene, is added to the mixture, and the organic phase is worked up in a customary manner by washing, drying and removing the solvent by distillation.

The compounds of the general formula I are usually obtained in the form of oils which frequently cannot be distilled without decomposition, but the last volatile constituents are removed by so-called "incipient distillation", that is to say by prolonged heating at moderately elevated temperatures under reduced pressure, and the compounds are purified in this manner. The refractive index serves to characterize them.

As already mentioned several times, the compounds of the general formula I which can be obtained according to the invention are distinguished by an excellent insecticidal, acaricidal and nematicidal action. They are active against plant, public health and store pests and in the veterinary medical sector. While their phytotoxicity is low, they have good activity against both sucking and biting insects and mites.

For this reason, the compounds of the general formula I which can be obtained according to the invention can be used successfully as agents to combat pests in plant protection and in the public health, store-protection and veterinary sectors.

Many of the compounds which can be obtained according to the invention and their use are known and are described in, for example, DE-OS (German Published Specification) No. 2,643,262, U.S. Pat. No. 4,127,652, European Pat. No. A 0,009,566, U.S. Pat. No. 4,325,948, U.S. Pat. No. 4,444,764 and U.S. Pat. No. 4,429,125.

As already explained above, it is possible using process steps (a) to (c) of the process according to the invention to prepare the valuable compounds of the general formula I in smooth reactions and in a straightforward manner, the overall yields obtained being excellent. The process (a) to (c) according to the invention surprisingly opens up, due to the specific combination of the process steps and due to the use in parts of new compounds which are produced in them, a way to allow preparation of the compounds of the general formula I at a favorable cost which has not hitherto been achievable. Since the individual intermediates are stable and, in the particular case where they are isolated, can be stored for a prolonged period, the process according to the invention also permits extremely great flexibility in production so that, if there is a sudden demand for the final products, manufacture to meet the demand is possible, and this can be of very great importance, especially due to the climate-related great seasonal variations in the plant-protection area.

In the following text, the process (and process steps) and compounds according to the invention are to be illustrated by the preparation examples which follow:

I. Process for the preparation of the compounds of the general formula VII (or II, with $R^3=CH_3-CHOR^4-$)

EXAMPLE I/1

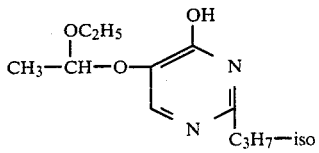

A mixture of 132 g (1 mole) of butyl glycolate, 72 g (1 mole) of ethyl vinyl ether and 0.3 g of p-toluenesulphonic acid is allowed to react to completion at a maximum of 40° C., cooling slightly. After the exothermic reaction has finished, the mixture is stirred at 40° C. for 2 hours, then, at 20° C., first 90 g (1.5 moles) of methyl formate and then, with slight cooling, at 20° C. 62 g (1.15 moles) of sodium methylate powder are added in portions. The reaction mixture is then stirred at 20° C. for 1½ hours and subsequently 211 g (1 mole) of methanolic sodium methylate solution and 122.5 g (1 mole) of isobutyramidine hydrochloride are added. The mixture is then stirred without cooling for 18 hours, the solvent is removed by distillation in vacuo, and the residue is dissolved in 500 ml of water. The remaining organic solvent is removed from the solution in vacuo at 40° C., and then 66 g (1.1 moles) of glacial acetic acid are added at 5° C. The product which has crystallized out is filtered off with suction and washed with water.

181.7 g (80% of theory) of 5-(1-ethoxyethoxy)-4-hydroxy-2-i-propylpyrimidine are obtained in the form of a colorless powder having a melting point of 70° C.

In analogy to Example 1, for example the following compounds of the formula VII are obtained:

TABLE 5

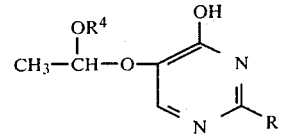

| Example No. | $-R^4$ | R | Yield (% of theory) | Physical constants |
|---|---|---|---|---|
| I/2 | $C_2H_5$ | tert.-$C_4H_9$ | 83 | m.p.: 104–105° C. |
| I/3 | $C_2H_5$ | $-CH_2-S-CH_3$ | 98 | $n_D^{26}$: 1.5441 |
| I/4 | $C_2H_5$ | 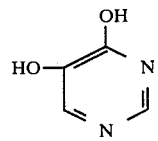 | 83 | m.p.: 115° C. |

Ia. Process for the preparation of the compounds of the general formula II ($R^3=H$)

EXAMPLE Ia/1

A mixture of 132 g (1 mole) of butyl glycolate, 72 g (1 mole) of ethyl vinyl ether and 0.3 g of p-toluenesulphonic acid is allowed to react to completion at a maximum of 40° C., cooling slightly. After the exothermic reaction has finished, the mixture is stirred at 40° C. for 2 hours, then, at 20° C., first 90 g (1.5 moles) of methyl formate and then, with slight cooling, at 20° C. 62 g (1.15 moles) of sodium methylate powder are added in portions. The reaction mixture is then stirred at 20° C. for 1½ hours and subsequently 211 g (1 mole) of methanolic sodium methylate solution and 80.6 g (1 mole) of formamidine hydrochloride are added. The mixture is then stirred without cooling for 18 hours, the solvent is removed by distillation in vacuo, and the residue is dissolved in 500 ml of water. Remaining organic solvent is removed from the solution in vacuo at 40° C., and concentrated hydrochloric acid is added to pH 2. The mixture is then stirred at 40° C. for 2 hours, and dilute sodium hydroxide solution is added until the pH reaches 5, and the mixture is then cooled to 5° C. The precipitated product is filtered off with suction and washed with a little cold water.

63 g (56% of theory) of 4,5-dihydroxypyrimidine are thus obtained in the form of a colorless powder having a melting point of 253° C.

EXAMPLE Ia/2

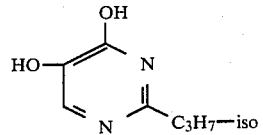

Water is distilled out of a solution of 168 g (1 mole) of 4-hydroxy-5-methoxy-2-i-propylpyrimidine and 350 ml of 48% strength hydrobromic acid until the boiling point has risen to 120° C. The mixture is then heated under reflux for 18 hours, the excess hydrobromic acid is removed by distillation in vacuo, and the residue is dissolved in 300 ml of water. The solution is adjusted to pH 5 at 5°–10° C. using concentrated sodium hydroxide solution, and the precipitated product is filtered off with suction.

In this manner, 149 g (97% of theory) of 4,5-dihydroxy-2-i-propylpyrimidine are obtained in the form of a beige powder having a melting point of 187° C.

In analogy to Example Ia/1 and Ia/2, for example the following compounds of the formula II are obtained:

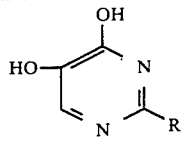

| Example No. | R | Melting point (°C.) |
|---|---|---|
| Ia/3 | tert.-C$_4$H$_9$ | 239 |
| Ia/4 | CH$_3$ | >250 |
| Ia/5 | CH$_2$—SO$_2$—CH$_3$ | 284 (decomposition) |

Ib. Process for the preparation of the starting materials of the formula VI

EXAMPLE Ib/1

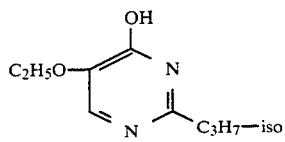

A suspension of 21.6 g (0.4 mole) of sodium methylate, 24.5 g (0.2 mole) of iso-butylamidine hydrochloride and 32 g (0.2 mole) of ethyl formylethoxyacetate is heated under reflux for 6 hours. The mixture is then evaporated and the residue is taken up in 200 ml of water. Concentrated hydrochloric acid is added to the aqueous phase, cooling in ice, until the pH is 6, and then the aqueous phase is extracted twice with 200 ml of methylene chloride each time. The combined methylene chloride extracts are dried over sodium sulphate and concentrated.

22 g (60.5% of theory) of 5-ethoxy-4-hydroxy-2-i-propylpyrimidine are obtained in the form of colorless crystals of melting point 154° C.

In analogy to Example Ib/1, for example the following compounds of the formula VI are obtained:

TABLE 6

| | | OH | (VI) |

R$^5$O—[pyrimidine structure]—R

| Example No. | R$^5$ | R | Melting point (°C.) |
|---|---|---|---|
| Ib/2 | i-C$_3$H$_7$ | i-C$_3$H$_7$ | 108–109 |
| Ib/3 | C$_2$H$_5$ | CH$_3$ | 160 |
| Ib/4 | CH$_3$ | i-C$_3$H$_7$ | 167 |
| Ib/5 | CH$_3$ | CH$_3$ | 206 |
| Ib/6 | C$_2$H$_5$ | CH$_3$ | 170 |
| Ib/7 | CH$_3$ | C$_2$H$_5$ | 168 |
| Ib/8 | C$_2$H$_5$ | H | 137 |

II. Process for the preparation of the compounds of the general formula III (process step (a))

EXAMPLE II/1

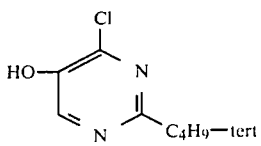

173 g (1.75 moles) of phosgene are passed into a mixture of 1 l of chloroform and 128 g (1.75 moles) of dimethylformamide at 5° C. While cooling further, 168g (1 mole) of 2-tert.-butyl-4,5-dihydroxypyrimidine are added in portions so that the reaction temperature does not exceed 20° C. The mixture is then stirred at 20° C. for 3 hours and thereafter, with cooling to a maximum of 10° C., first 200 ml of water and then 1,000 g of 45% strength sodium hydroxide solution are added dropwise. The aqueous phase is separated off, residues of chloroform are removed in vacuo, and then, at 10° C., the pH is adjusted to 6 by addition of concentrated hydrochloric acid. The precipitated product is filtered off with suction and washed with water.

172 g (92% of theory) of 2-tert.-butyl-4-chloro-5-hydroxypyrimidine are obtained in the form of a pale beige powder having a melting point of 108° C.

EXAMPLE II/2

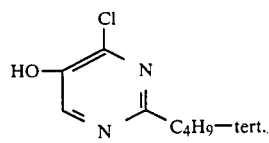

19.8 g (0.2 mole) of phosgene are passed into a mixture of 80 g of methylene chloride and 14.6 g (0.2 mole) of dimethylformamide at 5° C. While cooling further, 24 g (0.1 mole) of 2-tert.-butyl-5-(1-ethoxyethoxy)-4-hydroxypyrimidine are added in portions so that the reaction temperature does not exceed 20° C. The mixture is then stirred at 20° C. for 3 hours and, with cooling to a maximum of 10° C., first 45 ml of water and then 45 g of 45% strength sodium hydroxide solution are added dropwise. The aqueous phase is separated off, residues of methylene chloride are removed in vacuo, and then, at 10° C., the pH is adjusted to 6 by addition of concentrated hydrochloric acid. The precipitated product is filtered off with suction and washed with water.

15.7 g (84% of theory) of 2-tert.-butyl-4-chloro-5-hydroxypyrimidine are obtained in the form of a pale beige powder having a melting point of 108° C.

In analogy to Examples II/1 or II/2, for example the following compounds of the formula III are obtained:

TABLE 7

| Example No. | R | Physical constants |
|---|---|---|
| II/3 | C$_3$H$_7$—i | m.p. 105–107° C. |
| II/4 | CH$_3$ | m.p. 73° C. |

III. Process for the preparation of the compounds of the general formula IV (process step (b))

EXAMPLE III/1

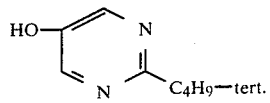

A solution of 186.5 g (1 mole) of 2-tert.-butyl-4-chloro-5-hydroxypyrimidine and 84 g (2.1 moles) of sodium hydroxide in 800 ml of water is hydrogenated at 50° C. under a pressure of hydrogen of 10 bar, in the presence of 15 g of Raney nickel. After uptake of hydrogen is complete, the catalyst is filtered off with suction. Concentrated hydrochloric acid is added to the filtrate until the pH reaches 4. The precipitated product is filtered off with suction and washed with water.

In this manner, 110 g (77% of theory) of 2-tert.-butyl-5-hydroxypyrimidine are obtained in the form of a colorless powder having a melting point of 132° C.

In analogy to Example III/1, the following compounds of the formula IV are obtained

TABLE 8

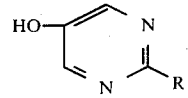
(IV)

| Example No. | R | Melting point [°C.] |
|---|---|---|
| III/2 | $C_3H_7-n$ | 117 |
| III/3 | H | 216 |
| III/4 | $CH_3$ | 173 |
| III/5 | $N(CH_3)_2$ | 164 |
| III/6 | $C_2H_5$ | 149 |
| III/7 | ⟨H⟩ (cyclohexyl) | 165 |

TABLE 8-continued (IV)

| Example No. | R | Melting point [°C.] |
|---|---|---|
| III/8 | phenyl | 145 |

IV. Process for the preparation of the compounds of the general formula I (process step (c))

EXAMPLE IV/1

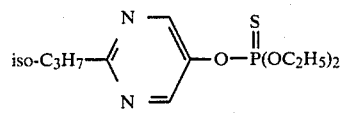

A mixture of 300 ml of acetonitrile, 13.8 g (0.1 mole) of 2-iso-propyl-5-hydroxypyrimidine, 20.7 g (0.15 mole) of potassium carbonate and 18.8 g (0.1 mole) of O,O-diethyl thionophosphoric chloride is stirred at 45° C. for 2 hours. The reaction mixture is poured into 400 ml of toluene and this is washed twice with 300 ml of water each time. The toluene solution is dried over sodium sulphate and evaporated in vacuo. The residue is subjected to incipient distillation under high vacuum. 17.4 g (62% of theory) of O,O-diethyl O-[2-iso-propyl-5-pyrimidinyl]thionophosphate are thus obtained in the form of a brown oil having refractive index $n_D^{21}$: 1.4970.

In an analogous manner, the following compounds of the formula

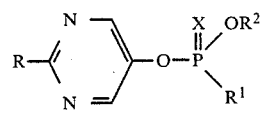
(I)

can be prepared:

TABLE 9

| Example No. | $R^2$ | $R^1$ | R | X | Yield (% of theory) | Refractive index: |
|---|---|---|---|---|---|---|
| IV/2 | $C_3H_7-iso$ | $CH_3$ | $C_3H_7-iso$ | S | 74 | $n_D^{21}$: 1.5102 |
| IV/3 | $CH_3$ | $OCH_3$ | $C_3H_7-iso$ | S | 66 | $n_D^{24}$: 1.5080 |
| IV/4 | $C_2H_5$ | $SC_3H_7-n$ | $C_3H_7-iso$ | S | 69 | $n_D^{26}$: 1.5284 |
| IV/5 | $C_2H_5$ | phenyl | $C_3H_7-iso$ | S | 74 | $n_D^{26}$: 1.5570 |
| IV/6 | $C_2H_5$ | $OC_2H_5$ | $C_3H_7-iso$ | O | 82 | $n_D^{32}$: 1.4630 |
| IV/7 | $C_2H_5$ | $NH-C_3H_7-iso$ | $C_3H_7-iso$ | S | 57 | $n_D^{32}$: 1.5057 |
| IV/8 | $C_3H_7-n$ | $OC_2H_5$ | $C_3H_7-iso$ | S | 73 | $n_D^{32}$: 1.4929 |
| IV/9 | $C_2H_5$ | $OC_2H_5$ | $CH_3$ | S | 92 | $n_D^{32}$: 1.4992 |
| IV/10 | $C_2H_5$ | $C_2H_5$ | $CH_3$ | S | 80 | $n_D^{32}$: 1.5169 |
| IV/11 | $C_2H_5$ | $OC_2H_5$ | phenyl | S | 80 | $n_D^{32}$: 1.5643 |

TABLE 9-continued

| Example No. | $R^2$ | $R^1$ | R | X | Yield (% of theory) | Refractive index: |
|---|---|---|---|---|---|---|
| IV/12 | $C_2H_5$ | $C_2H_5$ | 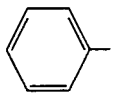 | S | 80 | $n_D^{32}$: 1.5827 |
| IV/13 | $C_2H_5$ | $OC_2H_5$ | H | S | 72 | $n_D^{32}$: 1.5028 |
| IV/14 | $C_2H_5$ | $OC_2H_5$ | $C_2H_5$ | S | 84 | $n_D^{20}$: 1.5014 |
| IV/15 | $C_2H_5$ | $OC_2H_5$ | $C_3H_7$—n | S | 60 | $n_D^{26}$: 1.4833 |
| IV/16 | $C_2H_5$ | $OC_2H_5$ | $C_4H_9$—n | S | 94 | $n_D^{21}$: 1.4958 |

EXAMPLE IV/17

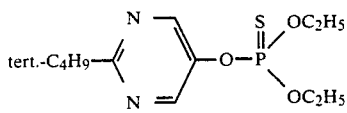

A mixture of 132 g (1 mole) of butyl glycolate, 72 g (1 mole) of ethyl vinyl ether and 0.3 g of p-toluenesulphonic acid is allowed to react to completion at a maximum of 40° C., cooling slightly. After the exothermic reaction has finished, the mixture is stirred at 40° C. for 2 hours, then, at 20° C., first 90 g (1.5 moles) of methyl formate and then, with slight cooling, at 20° C. 62 g (1.15 moles) of sodium methylate powder are added in portions. The reaction mixture is then stirred at 20° C. for 1½ hours and subsequently 211 g (1 mole) of methanolic sodium methylate solution and 136.5 g (1 mole) of t.-butyramidine hydrochloride. The mixture is then stirred without cooling for 18 hours, and 120 ml of concentrated hydrochloric acid are added and the mixture is then stirred at about 50° C. for 1 hour. The solvent is then removed by distillation in vacuo. The solid residue is dried in air and added in portions, at 20° C., to a mixture of 850 ml of chloroform, 109.5 g (1.5 moles) of dimethylformamide and 148.5 g (1.5 moles) of phosgene. The reaction mixture is then stirred at 20° C. for 2 hours and then, with cooling at 0°–10° C., a mixture of 435 g of 45 percent sodium hydroxide solution and 800 ml of water are added dropwise. The aqueous phase is separated off, residues of chloroform are removed in vacuo, and then hydrogenation is carried out at 50° C. and under a pressure of 10 bar of hydrogen, in the presence of 15 g of Raney nickel. After uptake of hydrogen is complete, the catalyst is filtered off with suction. Concentrated hydrochloric acid is added to the filtrate until pH 4 is reached. The precipitated product is filtered off with suction and washed with water. After drying, it is added to a mixture of 300 ml of acetonitrile, 124.2 g (0.9 mole) of potassium carbonate and 116.9 g (0.62 mole) of O,O-diethyl thionophosphoric chloride, and the mixture is stirred at 45° C. for 2 hours. The solvent is then removed by distillation in vacuo, the residue is dissolved in 400 ml of toluene, and the solution is washed twice with 300 ml of water each time. The toluene solution is dried over sodium sulphate and evaporated in vacuo. The residue is subjected to incipient distillation under high vacuum. 185 g (61% of theory) of O,O-diethyl O-[2-tert.-butyl-5-pyrimidinyl]thionophosphate are thus obtained in the form of a brown oil having a refractive index $n_D^{26}$: 1.4902.

EXAMPLE IV/18

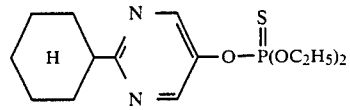

A mixture of 300 ml of acetonitrile, 17.8 g (0.1 mole) of 2-cyclohexyl-5-hydroxypyrimidine, 20.7 g (0.15 mole) of potassium carbonate and 18.8 g (0.1 mole) of O,O-diethyl thionophosphoric chloride is stirred at 45° C. for 2 hours. The reaction mixture is then poured into 400 ml of toluene and this is washed twice with 300 ml of water each time. The toluene solution is dried over sodium sulphate and evaporated in vacuo. The residue is subjected to incipient distillation under high vacuum. 21.7 g (66% of theory) of O,O-diethyl O-(2-cyclohexyl-5-pyrimidinyl)thionophosphate are thus obtained in the form of a brown oil having refractive index $n_D^{23}$: 1.5158.

In an analogous manner, the following compounds of the formula

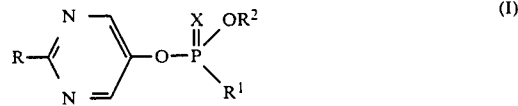                                    (I)

can be obtained:

TABLLE 10

| Example No. | $R^2$ | $R^1$ | R | X | Yield (% of theory) | Physical data (Refractive index; melting point °C.) |
|---|---|---|---|---|---|---|
| IV/19 | $C_2H_5$ | $NH-C_3H_7-iso$ |  | S | 51 | $n_D^{23}$: 1.5246 |
| IV/20 | $CH_3$ | $OCH_3$ |  | S | 64 | $n_D^{23}$: 1.5287 |

TABLLE 10-continued

| Example No. | R² | R¹ | R | X | Yield (% of theory) | Physical data (Refractive index; melting point °C.) |
|---|---|---|---|---|---|---|
| IV/21 | $C_2H_5$ | $OC_2H_5$ |  | S | 78 | $n_D^{24}$: 1.5142 |
| IV/22 | $C_2H_5$ | $NH-C_3H_7-iso$ |  | S | 62 | 49 |
| IV/23 | $CH_3$ | $OCH_3$ |  | S | 43 | $n_D^{24}$: 1.5390 |
| IV/24 | $C_3H_7-n$ | $OC_2H_5$ |  | S | 71 | $n_D^{25}$: 1.5128 |
| IV/25 | $C_2H_5$ | $NH-C_2H_5$ |  | S | 74 | $n_D^{26}$: 1.5310 |
| IV/26 | $C_2H_5$ | $OC_2H_5$ |  | S | | |
| IV/27 | $C_2H_5$ | $OC_2H_5$ |  | S | | |
| IV/28 | $C_2H_5$ | $OC_2H_5$ |  | S | 80 | $n_D^{23}$: 1.5164 |
| IV/29 | $C_2H_5$ | $OC_3H_7-n$ |  | S | | |
| IV/30 | $C_2H_5$ | $CH_3$ |  | S | 72 | $n_D^{25}$: 1.5428 |
| IV/31 | $C_2H_5$ | $OC_2H_5$ |  | O | | |
| IV/32 | $C_2H_5$ | $NH-C_3H_7-iso$ |  | O | | |
| IV/33 | $C_2H_5$ |  |  | S | 74 | $n_D^{25}$: 1.5815 |
| IV/34 | $C_2H_5$ | $SC_3H_7-n$ |  | S | | |
| IV/35 | $C_2H_5$ |  | H | S | | |
| IV/36 | $C_2H_5$ | $NH-C_2H_5$ | H | S | 66 | $n_D^{23}$: 1.5329 |
| IV/37 | $C_2H_5$ | $SC_3H_7$ |  | O | | |
| IV/38 | $C_2H_5$ | $C_2H_5$ |  | S | | |

TABLLE 10-continued

| Example No. | $R^2$ | $R^1$ | R | X | Yield (% of theory) | Physical data (Refractive index; melting point °C.) |
|---|---|---|---|---|---|---|
| IV/39 | $CH_3$ | $C_2H_5$ | ▷ | S | | |
| IV/40 | $C_3H_7$—iso | $CH_3$ | ▷ | S | 67 | $n_D^{26}$: 1.5233 |
| IV/41 | $CH_3$ | $NH—C_3H_7$—iso | ▷ | S | | |
| IV/42 | $CH_3$ | $NH—CH_3$ | ▷ | S | 66 | $n_D^{26}$: 1.5460 |
| IV/43 | $C_2H_5$ | $NH—CH_3$ | ▷ | S | | |
| IV/44 | $CH_3$ | $NH—C_2H_5$ | ▷ | S | | |
| IV/45 | $C_2H_5$ | $NH—C_3H_7$—iso | ⬠ | S | 55 | $n_D^{23}$: 1.5247 |
| IV/46 | $C_2H_5$ | $OC_2H_5$ | ▷-$CH_3$ | S | | |

EXAMPLE IV/47

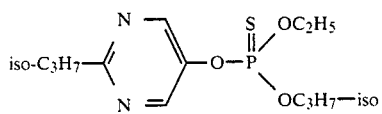

A mixture of 300 ml of acetonitrile, 13.8 g (0.1 mole) of 5-hydroxy-2-iso-propylpyrimidine, 20.7 g (0.15 mole) of potassium carbonate and 20.2 g (0.1 mole) of O-ethyl O-iso-propyl thionophosphoric chloride is stirred at 45° C. for 2 hours. The reaction mixture is then poured into 400 ml of toluene and this is washed twice with 300 ml of water each time. The toluene solution is dried over sodium sulphate and evaporated in vacuo. The residue is subjected to incipient distillation under high vacuum.

28 g (92% of theory) of O-ethyl O-iso-propyl O-(2-iso-propyl-5-pyrimidinyl)thionophosphate are thus obtained in the form of a yellow oil having refractive index $n^{23}$: 1.4910.

In an analogous manner, the following compounds of the formula

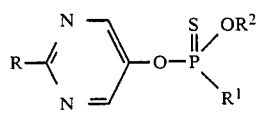

(I)

can be prepared:

TABLE 11

| Example No. | R | $R^2$ | $R^1$ | Refractive index |
|---|---|---|---|---|
| IV/48 | $—C_3H_7$—iso | $—C_3H_7$—iso | $—OC_3H_7$—iso | $n_D^{20}$: 1.4869 |
| IV/49 | $—C_4H_9$—tert. | $—C_2H_5$ | $—OC_3H_7$—iso | $n_D^{20}$: 1.4917 |
| IV/50 | $—C_3H_7$—iso | $—C_2H_5$ | $—OC_4H_9$—sec. | $n_D^{20}$: 1.4960 |
| IV/51 | $—C_4H_9$—tert. | $—C_2H_5$ | $—OC_4H_9$—sec. | $n_D^{22}$: 1.4935 |
| IV/52 | $—C_4H_9$—tert. | $—C_3H_7$—iso | $—OC_3H_7$—iso | $n_D^{22}$: 1.4857 |
| IV/53 | —⌬ | $—C_2H_5$ | $—OC_3H_7$—iso | $n_D^{22}$: 1.5516 |
| IV/54 | $—C_4H_9$—tert. | $—C_2H_5$ | $—NHC_2H_5$ | $n_D^{21}$: 1.5100 |
| IV/55 | —⌬ | $—C_2H_5$ | $—OC_4H_9$—sec. | |
| IV/56 | —⌬ | $—C_3H_7$—iso | $—OC_3H_7$—iso | |
| IV/57 | $—C_3H_7$—iso | $—C_3H_7$—n | $—OC_3H_7$—n | $n_D^{23}$: 1.4915 |

It will be understood that the specification and examples are illustrative but not limitative of the present invention and that other embodiments within the spirit and scope of the invention will suggest themselves to those skilled in the art.

What is claimed is:

1. A process for the preparation of a compound of the formula

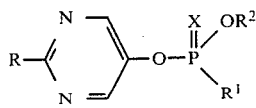

in which
R is hydrogen, alkoxy having 1 to 12 carbon atoms, monoalkylamino or dialkylamino having 1 to 6 carbon atoms in each alkyl moiety, alkyl which has 1 to 12 carbon atoms and is optionally substituted by $C_1$-$C_4$-alkoxy or $C_1$-$C_4$-alkylsulphonyl, cycloalkyl which has 3 to 8 carbon atoms and is optionally substituted by $C_1$-$C_4$-alkyl, and aryl which has 6 to 10 carbon atoms and is optionally substituted by $C_1$-$C_4$-alkyl, $C_1$-$C_4$-alkoxy or $C_1$-$C_4$-alkylsulphonyl, $R^1$ is $C_1$ to $C_6$-alkyl optionally substituted with $C_1$ to $C_4$-alkoxy, $C_1$ to $C_4$-alkylthio, halogen, cyano or nitro; alkylamino or dialkylamino having 1 to 6 carbon atoms in each alkyl moiety optionally substituted with $C_1$ to $C_4$-alkyl, $C_1$ to $C_4$-alkoxy, $C_1$ to $C_4$-alkylthio, halogen, cyano or nitro; $C_1$ to $C_6$ alkoxy optionally substituted with $C_1$ to $C_4$-alkyl, $C_1$ to $C_4$-alkoxy, $C_1$ to $C_4$-alkylthio, halogen, cyano or nitro; $C_1$ to $C_6$-alkylthio optionally substituted with $C_1$ to $C_4$-alkyl, $C_1$ to $C_4$-alkoxy, $C_1$ to $C_4$-alkylthio, halogen, cyano, or nitro; and phenyl, $R^2$ is $C_1$ to $C_6$-alkyl optionally substituted with $C_1$ to $C_4$-alkoxy, $C_1$ to $C_4$-alkylthio, halogen, cyano or nitro, and X is oxygen or sulphur, comprising (a) reacting a compound of the formula

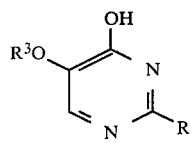

in which
$R^3$ is hydrogen or

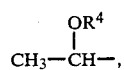

and
$R^4$ is $C_1$ to $C_4$-alkyl,
with a halogenating agent in the presence of an N,N-disubstituted amide at a temperature between 10° C. and 80° C., to produce a compound of the formula

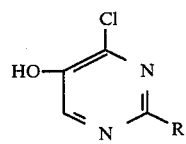

(b) reacting such compound with hydrogen in the presence of a hydrogenation catalyst, an acid acceptor and a diluent, at a temperature between 20° C. and 150° C., to produce a compound of the formula

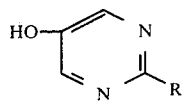

and then
(c) reacting such compound with a compound of the formula

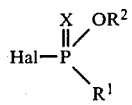

in which
Hal is halogen.

2. A process according to claim 1, in which
R is $C_1$-$C_4$-alkyl, $C_3$-$C_6$-cycloalkyl or phenyl,
$R^1$ is $C_1$-$C_4$-alkoxy,
$R^2$ is $C_1$-$C_4$-alkyl, and
X is sulphur.

3. A compound of the formula

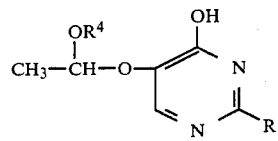

in which
R is hydrogen, alkoxy having 1 to 12 carbon atoms, monoalkylamino or dialkylamino having 1 to 6 carbon atoms in each alkyl moiety, alkyl which has 1 to 12 carbon atoms and is optionally substituted by $C_1$-$C_4$-alkoxy or $C_1$-$C_4$-alkylsulphonyl, cycloalkyl which has 3 to 8 carbon atoms and is optionally substituted by $C_1$-$C_4$-alkyl, and aryl which has 6 to 10 carbon atoms and is optionally substituted by $C_1$-$C_4$-alkyl, $C_1$-$C_4$-alkoxy or $C_1$-$C_4$-alkylsulphonyl, and
$R^4$ is $C_1$ to $C_4$-alkyl.

4. A compound according to claim 3, in which R is $C_1$-$C_4$ alkyl.

5. A process for the preparation of a compound according to claim 3, comprising reacting a hydroxyacetic ester of the formula

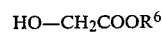

in which $R^6$ is $C_1$-$C_4$-alkyl,
with a vinyl ether of the formula

and with a formic ester of the formula

in which $R^7$ is $C_1$-$C_4$-alkyl,
in the presence of a base, and then with an amidine hydrochloride of the formula

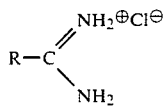

in which R is $C_1$–$C_4$-alkyl,
in the presence of a base and a diluent at a temperature between 15° C. and 60° C.

6. A process for the preparation of a compound of the formula

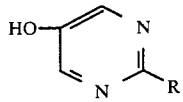

in which
R is hydrogen, alkoxy having 1 to 12 carbon atoms, monoalkylamino or dialkylamino having 1 to 6 carbon atoms in each alkyl moiety, alkyl which has 1 to 12 carbon atoms and is optionally substituted by $C_1$–$C_4$-alkoxy or $C_1$–$C_4$-alkylsulphonyl, cycloalkyl which has 3 to 8 carbon atoms and is optionally substituted by $C_1$–$C_4$-alkyl, and aryl which has 6 to 10 carbon atoms and is optionally substituted by $C_1$–$C_4$-alkyl, $C_1$–$C_4$-alkoxy or $C_1$–$C_4$-alkylsulphonyl,
comprising reacting a compound of the formula

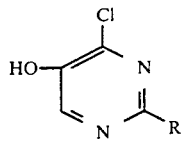

with hydrogen in the presence of a hydrogenation catalyst, an acid acceptor and a diluent at a temperature between 20° C. and 150° C.

* * * * *